United States Patent
Kozloski et al.

(10) Patent No.: US 9,349,100 B2
(45) Date of Patent: *May 24, 2016

(54) METHOD FOR PROVIDING A PROMPT FOR REAL-TIME COGNITIVE ASSISTANCE

(75) Inventors: James R. Kozloski, New Fairfield, CT (US); Clifford A. Pickover, Yorktown Heights, NY (US); Irina Rish, Rye Brook, NY (US)

(73) Assignee: International Business Machines Corporation, Armonk, NY (US)

( * ) Notice: Subject to any disclaimer, the term of this patent is extended or adjusted under 35 U.S.C. 154(b) by 496 days.

This patent is subject to a terminal disclaimer.

(21) Appl. No.: 13/599,248

(22) Filed: Aug. 30, 2012

(65) Prior Publication Data

US 2014/0067729 A1 Mar. 6, 2014

(51) Int. Cl.

| G06F 15/18 | (2006.01) |
|---|---|
| G06N 7/00 | (2006.01) |
| G06F 19/00 | (2011.01) |
| A61B 5/00 | (2006.01) |
| A61B 5/0476 | (2006.01) |

(52) U.S. Cl.
CPC ............ *G06N 7/005* (2013.01); *G06F 19/3481* (2013.01); *A61B 5/0476* (2013.01); *A61B 5/4088* (2013.01)

(58) Field of Classification Search
None
See application file for complete search history.

(56) References Cited

U.S. PATENT DOCUMENTS

| 6,236,968 | B1 | 5/2001 | Kanevsky et al. | |
|---|---|---|---|---|
| 6,632,174 | B1 | 10/2003 | Breznitz | |
| 7,881,936 | B2 * | 2/2011 | Longe et al. | 704/257 |
| 7,925,525 | B2 * | 4/2011 | Chin | 705/7.19 |
| 2007/0214416 | A1 * | 9/2007 | Lusty | 715/705 |
| 2008/0004926 | A1 | 1/2008 | Horvitz et al. | |
| 2009/0287678 | A1 | 11/2009 | Brown et al. | |
| 2010/0174533 | A1 * | 7/2010 | Pakhomov | 704/205 |
| 2010/0188230 | A1 | 7/2010 | Lindsay | |
| 2011/0070835 | A1 * | 3/2011 | Borras et al. | 455/41.2 |
| 2011/0258153 | A1 | 10/2011 | Kamar et al. | |
| 2011/0270117 | A1 | 11/2011 | Warwick et al. | |
| 2013/0138424 | A1 * | 5/2013 | Koenig et al. | 704/9 |

OTHER PUBLICATIONS

"Prediction and conversational momentum in an augmentative communication system", Norman Alm, John L. Arnott, Alan F. Newell, Communications of the ACM, vol. 35 Issue 5, May 1992, pp. 46-57.*

(Continued)

*Primary Examiner* — Kakali Chaki
*Assistant Examiner* — Mai T Tran
(74) *Attorney, Agent, or Firm* — Ryan, Mason & Lewis, LLP (57) ABSTRACT

Techniques for providing a prompt for real-time cognitive assistance. A method includes analyzing input from at least one environmental sensor to identify context information pertaining to a user situation, identifying a likely subsequent cognitive task of the user in the user situation based on the context information and use of a learned model, determining an action with respect to information to be suggested to the user via a corresponding prompt, wherein the determining is based on the likely subsequent cognitive task, the context information and information learned from at least one previous user situation, computing a confidence value to represent a level of certainty in the action, and providing the prompt to the user if the action has a confidence value greater than a threshold value corresponding to the action.

19 Claims, 2 Drawing Sheets

(56) References Cited

OTHER PUBLICATIONS

"The "Aware-System"—Prototyping an Augmentative Communication Interface", Lori K. Adams, Lisa M. Hunt, Melody M. Moore, RESNA 26th International Annual Conference, Technology & Disability: Research, Design, Practice & Policy, Jun. 19-Jun. 23, 2003, 4 pages.*

"Context-aware communication for severely disabled users", Adriane B. Davis, Melody M. Moore, Veda C. Storey, CUU '03 Proceedings of the 2003 conference on Universal usability, Nov. 10-11, 2003, pp. 106-111.*

Mihailidis et al. Context-aware assistive devices for older adults with dementia. Gerontechnology, vol. 2, 2002, pp. 173-188.

Mihailidis et al. The potential of intelligent technology as an occupational enabler. Occupational Therapy, 2005, pp. 22-23. Jan./Feb. 2005.

Chang et al. Context-aware Task Prompting System with Multiple Modalities for Individuals with Cognitive Impairments. ASSETS'08, Oct. 13-15, 2008. 2 pages.

Bharucha et al. Intelligent Assistive Technology Applications to Dementia Care : Current Capabilities, Limitations, and Future Challenges. Am J Geriatr Psychiatry. Feb. 2009; 17(2): 88-104.

LoPresti et al. Assistive technology for cognitive rehabilitation: State of the art. Neuropsychological Rehabilitation, 2004, 14 (1/2), 5-39.

Virone et al. Activity Prediction for In-home Activity Monitoring. 4th International Conference on Intelligent Environments, 2008 IET, Jul. 21-22, 2008.

The AI Behind Watson. http://www.aaai.org/Magazine/Watson/watson.php downloaded Aug. 30, 2012, 21 pages.

\* cited by examiner

FIG. 1

METHOD FOR PROVIDING A PROMPT FOR REAL-TIME COGNITIVE ASSISTANCE

FIELD OF THE INVENTION

Embodiments of the invention generally relate to information technology, and, more particularly, to machine learning technology.

BACKGROUND

Human cognitive ability, memory in particular, tends to decline with age, although the extent of the decline varies among individuals. Moreover, certain neurological disorders often associated with aging, such as Alzheimer's disease, can significantly affect cognitive abilities (and memory, in particular). For example, in early stages of Alzheimer's, a person can often perform everyday functions involving memory (for example, taking prescription medicine on time, remembering appointments, communicating with people, either face-to-face or over the phone), although such functions may become increasingly challenging as the disease progresses.

At more advanced stages of Alzheimer's, or even in the presence of normal age-related decline of cognitive abilities, a person may require assistance from other people in order to perform everyday cognitive tasks. The need for assistance can be directly correlated with challenge level of the task and the degree of decline in the individual. Commonly used scheduling and planning tools may not be helpful in such situations, because an individual may need a reminder to use the tools themselves. Moreover, such tools are not helpful in dynamically changing situations when a person needs to be reminded to take an action that depends on a previous sequence of actions (for example, going to a particular room to get a particular object and forgetting about this goal en route, etc.). Also, such tools cannot help an individual maintain a conversation in real-time when a person begins forgetting words.

In such situations, therefore, it would be desirable to equip a person with a real-time, adaptive cognitive digital assistant (CDA) that could evaluate the situation, recognize a cognitive task to be performed by a person using sensor inputs, and suggest an action (a word, a reminder about an activity, etc.), while also being able to adapt to the particular person's cognitive issues, behavior, and situations arising in the person's environment.

Moreover, such a need exists in settings beyond those detailed above, because even individuals without cognitive decline (for example, the general population, including young and healthy individuals) can engage in cognitive tasks that are highly challenging, and could potentially utilize such CDA for memory extending reminders and improved decision-making. Existing approaches, however, suffer from a poor ability to recognize the context of a user and deploy assistive aids in an adaptive fashion.

SUMMARY

In one aspect of the present invention, techniques for human memory enhancement using machine learning are provided. An exemplary computer-implemented method for providing a prompt for real-time cognitive assistance can include steps of analyzing input from at least one environmental sensor to identify context information pertaining to a user situation, identifying a likely subsequent cognitive task of the user in the user situation based on the context information and use of a learned model, determining an action with respect to information to be suggested to the user via a corresponding prompt, wherein the determining is based on the likely subsequent cognitive task, the context information and information learned from at least one previous user situation, computing a confidence value to represent a level of certainty in the action, and providing the prompt to the user if the action has a confidence value greater than a threshold value corresponding to the action.

Another aspect of the invention or elements thereof can be implemented in the form of an article of manufacture tangibly embodying computer readable instructions which, when implemented, cause a computer to carry out a plurality of method steps, as described herein. Furthermore, another aspect of the invention or elements thereof can be implemented in the form of an apparatus including a memory and at least one processor that is coupled to the memory and operative to perform noted method steps. Yet further, another aspect of the invention or elements thereof can be implemented in the form of means for carrying out the method steps described herein, or elements thereof; the means can include (i) hardware module(s), (ii) software module(s), or (iii) a combination of hardware and software modules; any of (i)-(iii) implement the specific techniques set forth herein, and the software modules are stored in a tangible computer-readable storage medium (or multiple such media).

These and other objects, features and advantages of the present invention will become apparent from the following detailed description of illustrative embodiments thereof, which is to be read in connection with the accompanying drawings.

DETAILED DESCRIPTION

As described herein, an aspect of the present invention includes implementing a cognitive digital assistant (CDA) for human memory enhancement using machine learning. Accordingly, at least one embodiment of the invention includes leveraging machine learning techniques to aid individuals with cognitive difficulties, specifically memory or other context-awareness issues, by providing prompts to the individual. Such prompts are selected and deployed in real-time through adaptive user interfaces and allow an individual to, for example, complete a sentence, recognize another individual, move through an otherwise familiar environment, etc. In an example embodiment of the invention, the prompts are generated by a learning component that draws upon information gathered from the user, other individuals such as caregivers, and wider data sources such as the Internet.

In at least one embodiment of the invention, the CDA makes use of a profile stored on the device that specifies various aspects of a user, such as, for example, state of the user's disease (advanced versus mild, etc.), nationality of the user, geography, language of the user, employment of the user, manually input word combinations, etc. At least one embodiment of the invention can also include generating and incorporating a confidence level and a situation-assessment component (SAC) to assess a current situation or a likely forecasted situation for the user. A confidence level can be computed using artificial intelligence tools such as, for example, probabilistic inference in multivariate probabilistic models. By way of example, given several known variables such as personal information about the user/patient (for example, the names of his or her relatives) and some context-specific information from a particular conversation, the CDA can use probabilistic inference to estimate a probability that the user is talking about a particular person. If the user cannot remember the name of the person, the CDA can possibly determine that name provided that the probability/confidence is high enough. If no name is assigned a sufficiently high probability/confidence level, the CDA may refrain from any suggestions because the situation is too uncertain, or the CDA may start suggesting multiple names from the list.

Use of a computed confidence level can trigger an action-taking component of the CDA to take an action and prompt the user when the confidence level of a potential action exceeds a threshold value. The threshold value is initially set to a default value by the CDA, but the value can be tuned automatically based on the feedback from the user and/or caregiver. For example, if the reminders become too frequent or annoying for the user, the threshold can be increased in order to avoid unnecessary suggestions. Similarly, if the reminders are too infrequent and the patient is becoming increasingly forgetful, the threshold may need to be lowered. Also, the CDA allows direct setting of the confidence parameter by the user and/or caregiver. Different types of actions may have different initial thresholds; moreover, as described above, the thresholds can be changing based on the feedback for each action. This, for example, can facilitate real-time and continuous monitoring of a user's context and need, allowing reminders to be deployed whenever a user encounters a temporary cognitive deficit, such as the inability to complete a sentence or remember a name.

The CDA, which supports a user's cognitive functions such as memory and decision-making ability, can include, in at least one embodiment of the invention, multiple components such as follows. The CDA can include a set of electronic audio and/or video sensors to observe the environment and the behavior of an individual (the user or surrounding individuals). Also, the CDA can include a machine-learning component that assesses and records the situation and needs of the user. By way of example, while receiving inputs from a phone conversation on a particular topic, the CDA notes that a person cannot remember certain words to continue certain sentences, and the CDA records the future need for quick reminders of the word or words that the user most likely has in mind for the particular context. A machine-learning component can also adapt to novel situations and to the changing needs and goals of the user, as well as provide real-time suggestions and reminders.

Further, the CDA can include a mechanism capable of receiving direct input from an individual (the user and/or another person) or another CDA (for example, from a caregiver or spouse's CDA) to provide additional information to the system and/or correct actions suggested by the CDA. By way of example, when situations and needs have never previously been observed by the CDA and the system cannot make inference from its prior knowledge and data to generate a suggested action, human inference can be incorporated.

Additionally, in at least one embodiment of the invention, the CDA can perform an analysis of word combinations and/or associations of a user, along with determining and analyzing word combinations used by common surrounding individuals (such as family members, co-workers, etc.), words used in a particular place of businesses, and other user-related sources.

Figure 1:
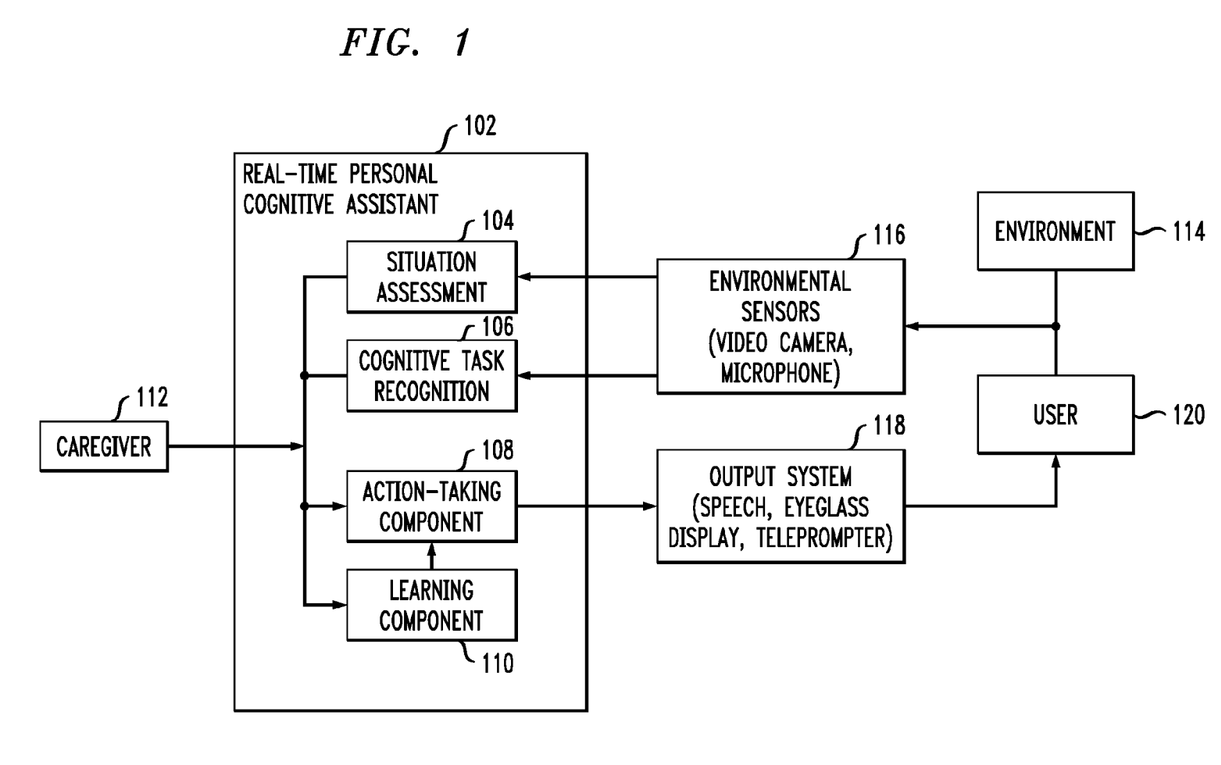
FIG. 1 is a block architecture diagram illustrating an example embodiment, according to an aspect of the invention.

FIG. 1 is a block architecture diagram illustrating an example embodiment, according to an aspect of the invention. By way of illustration, FIG. 1 depicts a real-time personal cognitive assistance (also referred to as the CDA herein) 102, as well as related components and influencing entities. For example, FIG. 1 depicts environmental sensors 116 that are capable of receiving audio, video and other type of input that can be provided to CDA 102 to be used to identify the state of the environment 114 as well as the cognitive state of the user 120 (for example, via brain wave activity, an electroencephalogram (EEG), etc.). At least one embodiment of the invention can incorporate the use of video, speech-to-text data, as well as a computer-human interface device. Further, at least one embodiment of the invention can additionally receive input from another user or a caregiver 112.

As also depicted in FIG. 1, the CDA 102 includes a situation assessment component (SAC) 104, which uses a learned model and input from the sensors 116 to identify the state of the environment 114. Additionally, a cognitive task recognition component 106 uses a learned model and input from the sensors 116 to identify the current cognitive state of the user 120 (as well as the likely necessary cognitive task). In at least one embodiment of the invention, the learned model contains information about (1) the variables describing the user's cognitive states, the user's environment, and the user's potential actions, as well as (2) information about relations among those variables and actions (the relations are quantitative, associated with probability distributions describing the likelihood of some variables given the other variables). Examples of cognitive variables can include being focused or distracted, being in a positive or negative mood, emotional state, as well as a current cognitive task the user is trying to complete (saying a sentence, searching for an object, etc.). Examples of environment-describing variables can include being at home, being in a car, being alone or with other people, etc. Further, examples of actions can include a particular word to complete a sentence, picking up a key before leaving the house, turning on and off appliances at home, etc. The cognitive task recognition component 106 uses observations of some variables to make inferences about other variables, wherein the inference includes computing probabilities of unobserved variables (for example, cognitive states) given observations of other variables, such as behavioral and environmental variables.

Particularly, at least one embodiment of the invention includes using the Bayesian approach to making inferences from the data and updating the current model. Bayesian reasoning is a probabilistic approach to inference based on combining prior knowledge with observed data using the Bayes rule where: P(H) is the prior probability of hypothesis H, P(D) is the prior probability of observing data D, P(D|H), referred to as the likelihood, is the probability of observing D if hypothesis H holds, and P(H|D) is the posterior probability of H after observing data D.

A common framework for Bayesian reasoning includes graphical probabilistic models, for example, Bayesian networks. Bayesian networks, also called belief networks, provide a graphical framework for compact representation of multivariate probabilistic distributions and for efficient reasoning techniques. A Bayesian network is a directed acyclic graph, where the nodes represent random variables of interest (for example, the current speech pattern and word choice of a user) and the edges denote probabilistic dependencies among the variables. More specifically, each node/variable is associated with a conditional probability given its parents in the network; that is, the nodes directly pointing to that node (below, Xi denote nodes, and Pa(i) denote the set of node's parents).

Further, FIG. 1 depicts a learning component 110 that includes a computer program for implementing machine-learning capabilities that allows the system to learn from previously observed situations and a person's past behavior, and adapt to the person's cognitive tasks, needs and environment. By way of example, at least one embodiment of the invention can include a speech-recognition unit that analyzes speech during a user conversation, and predicts words and/or phrases that the user likely intends to say but may not be able to remember. One approach, in accordance with at least one embodiment of the invention, to addressing the learning tasks includes using a classical reinforcement learning loop. In this respect, the system may enter the following cycle:

(1) The system operates in an "environment" which provides it with inputs that include observations of user's behavior and actions (speech data, video input, etc.), the time and location, other people involved in the current situation, etc.

(2) The system maps these inputs into a state of the user and his/her environment. The current state X is represented as a vector of state variables $X=(X1, \ldots, Xn)$. Herein, state variables can describe:

(a) various aspects describing a user's mental state (for example, the cognitive task he/she is performing (reading, writing, having a conversation, etc.)), cognitive state such as thinking of a particular person or place (inferred from his/her current conversation), and/or emotional state (tired, stressed, excited, confused, etc.);

(b) a user's environment, such as location (being at home, outside, etc.), current goals (for example, going to a doctor's appointment), the weather outside, etc.; and (c) general user profile (the names and other info about the user's relatives, the user's interests, likes and dislikes, the user's habits, the user's historic profile, including education, places he or she used to live, etc.).

(3) The learning agent interacts with the environment and the user (that is, obtains the inputs, which lead to the update in the observed states).

(4) The agent uses the inputs and a model of a user and an environment that describes relationships among the state variables and helps to predict future (unobserved) states to decide on the next user action. This set of all possible user actions at time T may be represented as $A(T)=\{A1, \ldots, An\}$.

(5) The agent receives feedback ('reward') for predicting each action in a form of a user's response specifying appropriateness of the current prediction; also, the agent can receive feedback on the 'long-term results' from the user and his/her caregivers.

(6) Based on the feedback received, the system can modify its model of the user (for example, his/her cognitive or emotional state variables) and the environment so that, in the future, the system can more accurately predict actions. As an example of a user model, at least one embodiment of the invention can include using a probabilistic graphical model such as a Bayesian network which includes multiple variables describing the user and his/her environment (as mentioned above), and probabilistic relationships among these variables, quantified by conditional probabilities of observing a particular value of the variable given the values of some other variables. The agent adaptively updates (learns) the model of the user and environment based on the feedback, comparing the actual feedback with the predictions made by the system.

(7) If the system realizes the current model is insufficient, at least one embodiment of the invention includes using an active learning or exploration step to elicit more information from a user and/or the environment.

The CDA 102 additionally includes an action-taking component 108, which decides on the next action to be sent to the user 120 via a prompt. The action-taking component 108 incorporates input from the SAC 104, the cognitive task recognition component 106, as well as the learning component 110. Also, FIG. 1 depicts an output system 118 (also referred to herein as a communication component) that produces an output prompt to communicate the decided-upon action to the user 120. For example, the output can be in various forms such as speech output, output to a teleprompter or screen, output to an eyeglass display, etc. By way of illustration, an example output prompt may include a suggestion of a most-likely word or a sequence of words to continue the sentence when the user experiences difficulties in a conversation. Another example prompt output might include a reminder about an action that the user intended to do but forgot.

As noted herein, in at least one embodiment of the invention, the CDA 102 can suggest words and/or phrases to a user based on an analysis of, for example, past word combinations and/or associations of a user, word combinations used in Internet sources and databases, word combinations used by family members or common acquaintances, and/or word combinations used in a place of business.

Accordingly, in an example embodiment of the invention, the CDA performs analysis and computation on a continuous stream of text input (in some cases, converted text input) from sensors such as a speech recognition sensor, a keyboard used by the user while at a computer or cell phone, etc. A microphone or audio sensor can also be used to detect speech input (of the user as well as surrounding individuals). Such analysis can, for example, attempt to complete sentences based on the input.

Further, in at least one embodiment of the invention, a confidence value is computed and updated at regular intervals to indicate a level of certainty that the system has in anticipating the next word or phrase. For example, if the user pauses to remember, and if sufficient information is available in the data stored for analysis, the confidence value should grow to some threshold. Note that confidence can grow because as a user struggles and takes time to continue speaking, a computational search algorithm uncovers more relationships in what has been said previously to adequately predict what will be or ought to be spoken next. If the user continues to pause, the confidence can grow as the calculation proceeds, until the threshold is reached. The confidence level can also grow as the system has time to search more databases and/or has time to search more deeply in a single database.

At this point, the action-taking component 108 can take action and prompt the user. The confidence level can be indicated, for example, by a visual indicator, an audio indicator, a textual change, a speech change (for instance, louder if more confident or switching to a different voice when more confident), etc.

Note that one or more embodiments of the invention need not be restricted to typical inputs such as a user's voice, but can also have applications to incorporate input from individuals with impaired voices or motor disorders, for example, through brain wave analysis, muscle twitches, etc. For instance, if a motor-disabled individual is grasping for a word, and a brainwave analysis and facial tic analysis suggests a certain likely word, this information may be applied to the selection of a suggested word by the CDA. For instance, note that the presence of a tic or stutter can be a strong cue as to the word that is to be spoken next. This occurs because often the same category of words (for example, words starting with the letter "f") causes the same category of speech difficulty among certain individuals.

In those instances where sufficient time is available to complete an analysis (due, for example, to the user's pausing to remember), but sufficient information is not available for the analysis to reach a criterion confidence threshold, active learning component 110 is triggered. The learning component 110 summarizes the situation and context and distributes this information electronically to a pre-configured set of advisors, family-members, and/or caregivers, whose responses are incorporated into the system's analysis data for future use.

The situation and context are described by variables that can take different values, for example, a variable describing the topic of conversation, a variable describing people involved, a variable describing current goal the user is trying to achieve (for instance, find a book or another item at home, make it on time for the doctor's appointment, etc.). The CDA can summarize the context/situation by providing a list of variables and their current values. Additionally, a mechanism for distributing this information to third parties can include, for example, sending an email or a text message to a third party cell phone or personal computer.

Also, at least one embodiment of the invention includes an active learning mechanism, which can function as follows. If, for example, in a probabilistic method, the computed probability distribution is too uncertain (for example, the probability of even the most-likely answer is lower than a confidence level threshold) or, alternatively, the entropy of the distribution is too high, then the system determines that it does not have enough information to make a sufficient decision about its next action, and the system can request more information from the user.

An active learning component is based on an information-theoretic approach that evaluates several possible requests for getting additional information (for example, additional measurements, or questions to the user) based on how informative the requests are with respect to the variable of interest that the system currently is uncertain about. By way of example, if the variable of interest, Y, corresponds to a particular word out of a list of words to suggest, and the current probability distribution P(Y) is too uncertain (the entropy H(Y) is too high), the system may need to request more information from caregivers about the user and a particular context or situation (for instance, if the user is trying to remember his/her friend's name). Also, among many variables describing the context of the conversation, there are the time and location where the events being discussed take place. The system evaluates each variable Z with respect to the expected decrease in the entropy of Y that Z can provide, that is, the mutual information I(Y:Z), and selects the most-informative variable Z about which to send a request. For example, the time or location may turn out to be more informative (for instance, if the 'time' relates to the user's high-school years, the search for the name of a friend is narrowed significantly) than many other variables from the user's profile (for instance, the variable describing the make of the user's car).

Aspects of the invention are further detailed via the following illustrative examples. A first example involves an elderly Alzheimer's patient speaking with a friend at a nursing home. The patient says, "My daughter's husband's father just had an accident. Thank goodness his son was there to help . . . you know who I mean . . . ," and then pauses. The CDA 102 analyzes the patient's words and attempts to complete the open-ended sentence with the name of the person to whom she is referring. However, in this example, the system has not yet learned that a daughter's husband's father's son is the same as a daughter's brother-in-law. Although the system knows that the patient's daughter's brother-in-law is named Harry, the system is not confident enough to prompt the patient (user) with that information. The system may know such information, for example, because it has encountered this relationship described in a user's email or because this relationship is learned from an analysis of twitter conversations, voice conversations, medical records, profiles, and/or other user recordings or documents. Such analysis may be done in an opt-in fashion (with permission granted by the user, caregiver, or guardian) to address privacy concerns.

Accordingly, continuing with the example above, the CDA 102 can send a follow-up question to the patient's caregiver: "Is a daughter's husband's father's son the same as a daughter's brother-in-law?" As detailed herein, messages can be transmitted via email or cell phone, and choosing which question to ask can be implemented using active learning methodology for selecting the next most informative variable for a query. The caregiver replies "yes," and from now on, the prompt is available from the CDA 102. Note also that such a prompt can be applied in a variety of other settings, such as composing a memoir, asking a physician a question about experienced symptoms, conducting a business transaction, interacting with a caregiver, etc.

In a second example, a patient's spouse has suggested that the patient is forgetting things more frequently. Fortunately, the patient has been using the memory enhancement CDA 102 for several years. The doctor reviews the records of prompts and confidence levels over that time and finds that, in fact, a marked drop-off in cognitive ability (or speech motor ability) in the patient began 8 months ago. The doctor can now tailor treatment to a patient who has been experiencing mild cognitive impairment for that time duration.

As also detailed herein, embodiments of the invention can include extensions of use in other areas or contexts. By way of example, aside from helping people with mild to severe cognitive impairment, the CDA 102 may be also useful for people with normal cognitive skills if they wish to enhance their communication abilities or emulate people they admire. As an example, a user may be giving a speech on computing technology. The user may pause, searching for an appropriate word. The CDA 102 can scan a database, the Internet, technical articles, and/or encyclopedias, and communicate a likely useful word or phrase to the user (for example, an audio communication via an ear-piece or visually via a text prompt on a teleprompter or on special eyeglasses).

Additionally, the situation assessment component (SAC) 104 can be used to assess a current situation or a likely forecasted situation for the user. For example, the CDA 102 may determine that the user is talking with family members (based on video or audio analysis), and thus, certain word associations would be appropriate. Also, the SAC 104 may determine that a user is in a home, a business, a restaurant, etc., and thus certain word associations would be appropriate. As described herein, at least one embodiment of the invention includes using probabilistic (Bayesian) inference to compute probabilities of unknown variables (such as, for example, a proper word to use) given observations of other variables and a probabilistic model (such as a Bayesian network) describing relationships among all variables of interest used to describe the user and situations he/she encounters. The relationships can be quantified by probabilities which can be specified in advance by an expert, and/or learned from data using machine-learning techniques such as learning structure and parameters of Bayesian networks.

Further, one or more embodiments of the invention can be implemented by users traveling in foreign countries to aid in determining appropriate word associations for that country or foreign language. Aspects of the invention can also be utilized when users are communicating with people of different cultures and ages who may use different word combinations, as well as when people from different industries or educational disciplines attempt to explain information to one another.

Additionally, at least one embodiment of the invention includes security mechanisms to preserve the privacy of the user or patient. For example, the system can be configured to only share data with certain individuals, or to only access an electronic living will of the patient in order to determine who should have access if the user is no longer capable of communicating this information.

Figure 2:
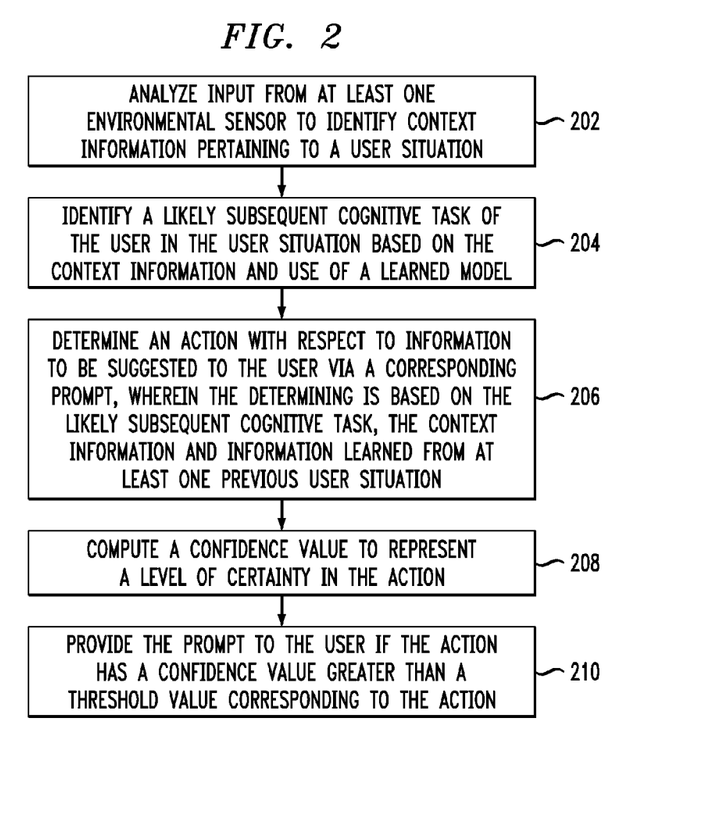
FIG. 2 is a flow diagram illustrating techniques for providing a prompt for real-time cognitive assistance, according to an embodiment of the invention.

FIG. 2 is a flow diagram illustrating techniques for providing a prompt for real-time cognitive assistance, according to an embodiment of the present invention. Step 202 includes analyzing input from at least one environmental sensor to identify context information pertaining to a user situation. As described herein, the input includes audio, video and/or text-based input.

Step 204 includes identifying a likely subsequent cognitive task of the user in the user situation based on the context information and use of a learned model. Identifying a likely subsequent cognitive task can include performing an analysis of word combinations and/or word associations of the user, analyzing word combinations used by additional individuals, as well as determining words commonly used in a particular context.

Step 206 includes determining an action with respect to information to be suggested to the user via a corresponding prompt, wherein the determining is based on the likely subsequent cognitive task, the context information and information learned from at least one previous user situation. Determining an action to be suggested can include incorporating input from at least one Internet source. Additionally, at least one embodiment of the invention includes implementing machine-learning capability to learn from at least one previously observed situation and the user's past behavior to adapt the determining step to a user's cognitive tasks and environment.

Step 208 includes computing a confidence value to represent a level of certainty in the action. The confidence value can be indicated via a visual indicator, an audio indicator, a textual change, and/or a speech change. Also, at least one embodiment of the invention includes updating the confidence value at a specified interval.

Step 210 includes providing the prompt to the user if the action has a confidence value greater than a threshold value corresponding to the action. As detailed herein, the prompt can include a speech or audio output and/or a visual output. Additionally, in at least one embodiment of the invention, the prompt is stored in a database.

Further, different types of actions may have different initial thresholds. As an example, the system may determine that the user is driving a car and requesting or needing directions. The confidence threshold may automatically be increased because giving an incorrect set of directions could be dangerous. On the other hand, the confidence threshold may be decreased for less significant scenarios, such as whispering into the user's ear the name of the user's favorite novelist. Additionally, the threshold value corresponding to the action can be modified based on feedback pertaining to the action.

The techniques depicted in FIG. 2 can also include analyzing user input to identify a cognitive state of the user. The user input can include, for example, brain wave activity and/or an electroencephalogram (EEG), as well as information from a stored user profile that specifies at least one aspect of the user. Aspects of the user includes a state of a user disease, nationality of the user, location of the user, language of the user, employment of the user, etc.

Additionally, at least one embodiment of the invention includes analyzing input provided by an individual (the user and/or an additional individual) to supplement identification of the user situation. Further, a learned model can be used and/or incorporated to identify a state of an environment involved in the user situation. Also, the techniques depicted in FIG. 2 can additionally include generating a summary of the user situation and the context information, and distributing the summary to a pre-configured set of individuals for feedback. Moreover, the feedback provided by the set of individuals can be incorporated in the determining step.

The techniques depicted in FIG. 2 can also, as described herein, include providing a system, wherein the system includes distinct software modules, each of the distinct software modules being embodied on a tangible computer-readable recordable storage medium. All of the modules (or any subset thereof) can be on the same medium, or each can be on a different medium, for example. The modules can include any or all of the components shown in the figures and/or described herein. In an aspect of the invention, the modules can run, for example, on a hardware processor. The method steps can then be carried out using the distinct software modules of the system, as described above, executing on a hardware processor. Further, a computer program product can include a tangible computer-readable recordable storage medium with code adapted to be executed to carry out at least one method step described herein, including the provision of the system with the distinct software modules.

Additionally, the techniques depicted in FIG. 2 can be implemented via a computer program product that can include computer useable program code that is stored in a computer readable storage medium in a data processing system, and wherein the computer useable program code was downloaded over a network from a remote data processing system. Also, in an aspect of the invention, the computer program product can include computer useable program code that is stored in a computer readable storage medium in a server data processing system, and wherein the computer useable program code is downloaded over a network to a remote data processing system for use in a computer readable storage medium with the remote system.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in a computer readable medium having computer readable program code embodied thereon.

An aspect of the invention or elements thereof can be implemented in the form of an apparatus including a memory and at least one processor that is coupled to the memory and operative to perform exemplary method steps.

Figure 3:
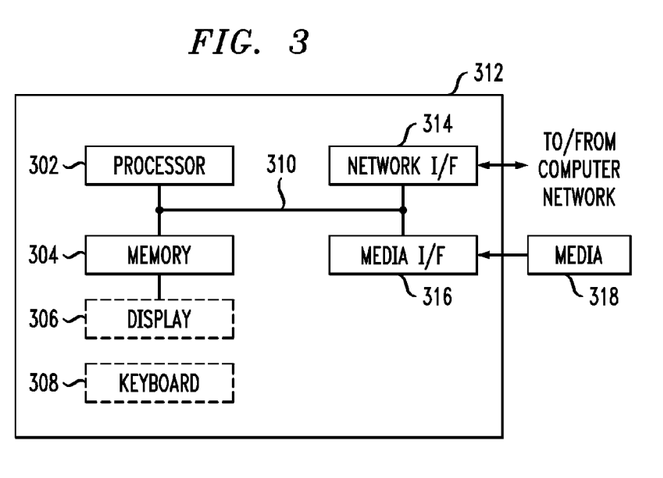
FIG. 3 is a system diagram of an exemplary computer system on which at least one embodiment of the invention can be implemented.

Additionally, an aspect of the present invention can make use of software running on a general purpose computer or workstation. With reference to FIG. 3, such an implementation might employ, for example, a processor 302, a memory 304, and an input/output interface formed, for example, by a display 306 and a keyboard 308. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, a mechanism for inputting data to the processing unit (for example, mouse), and a mechanism for providing results associated with the processing unit (for example, printer). The processor 302, memory 304, and input/output interface such as display 306 and keyboard 308 can be interconnected, for example, via bus 310 as part of a data processing unit 312. Suitable interconnections, for example via bus 310, can also be provided to a network interface 314, such as a network card, which can be provided to interface with a computer network, and to a media interface 316, such as a diskette or CD-ROM drive, which can be provided to interface with media 318.

Accordingly, computer software including instructions or code for performing the methodologies of the invention, as described herein, may be stored in associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 302 coupled directly or indirectly to memory elements 304 through a system bus 310. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 308, displays 306, pointing devices, and the like) can be coupled to the system either directly (such as via bus 310) or through intervening I/O controllers (omitted for clarity).

Network adapters such as network interface 314 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 312 as shown in FIG. 3) running a server program. It will be understood that such a physical server may or may not include a display and keyboard.

As noted, aspects of the present invention may take the form of a computer program product embodied in a computer readable medium having computer readable program code embodied thereon. Also, any combination of computer readable media may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the present invention may be written in any combination of at least one programming language, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. Accordingly, an aspect of the invention includes an article of manufacture tangibly embodying computer readable instructions which, when implemented, cause a computer to carry out a plurality of method steps as described herein.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, component, segment, or portion of code, which comprises at least one executable instruction for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the components detailed herein. The method steps can then be carried out using the distinct software modules and/or sub-modules of the system, as described above, executing on a hardware processor 302. Further, a computer program product can include a computer-readable storage medium with code adapted to be implemented to carry out at least one method step described herein, including the provision of the system with the distinct software modules.

In any case, it should be understood that the components illustrated herein may be implemented in various forms of hardware, software, or combinations thereof; for example, application specific integrated circuit(s) (ASICS), functional circuitry, an appropriately programmed general purpose digital computer with associated memory, and the like. Given the teachings of the invention provided herein, one of ordinary skill in the related art will be able to contemplate other implementations of the components of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of another feature, integer, step, operation, element, component, and/or group thereof.

The corresponding structures, materials, acts, and equivalents of all means or step plus function elements in the claims below are intended to include any structure, material, or act for performing the function in combination with other claimed elements as specifically claimed.

At least one aspect of the present invention may provide a beneficial effect such as, for example, incorporating an active learning capability that gathers information for improving the system's performance (for example, asking questions about the environment and/or user).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for providing a prompt for real-time cognitive assistance, the method comprising:
   analyzing input from at least one environmental sensor to identify context information pertaining to a user situation;
   forecasting a subsequent cognitive task of the user in the user situation based on the context information and use of a learned model;
   determining a combination of two or more words to be communicated by the user in anticipation of the user communicating said combination of two or more words, wherein the determining is based on the forecasted subsequent cognitive task, the context information and information learned from at least one previous user situation;
   computing a confidence value to represent a level of certainty in the combination of two or more words to be communicated by the user in connection with the forecasted subsequent cognitive task;
   updating the confidence value at a specified interval until the confidence value reaches a threshold value; and
   providing a prompt to the user, wherein said prompt contains the combination of two or more words to be communicated by the user, upon the confidence value reaching the threshold value;
   wherein at least one of the steps is carried out by a computer device.

2. The method of claim 1, wherein the threshold value corresponding to the combination of two or more words to be communicated by the user is modified based on feedback pertaining to the combination of two or more words to be communicated by the user.

3. The method of claim 1, further comprising:
   analyzing user input to identify a cognitive state of the user.

4. The method of claim 3, wherein the user input comprises brain wave activity or an electroencephalogram (EEG).

5. The method of claim 3, wherein the user input comprises information from a stored user profile that specifies at least one aspect of the user.

6. The method of claim 5, wherein the at least one aspect of the user includes a state of a user disease, nationality of the user, location of the user, language of the user, or employment of the user.

7. The method of claim 1, wherein the input includes audio, video or text-based input.

8. The method of claim 1, further comprising:
analyzing input provided by an individual to supplement identification of the user situation.

9. The method of claim 8, wherein the individual comprises the user or an additional individual.

10. The method of claim 1, further comprising:
using a learned model to identify a state of an environment involved in the user situation.

11. The method of claim 1, wherein said forecasting comprises performing an analysis of at least one word combination or word association of the user.

12. The method of claim 1, wherein said forecasting comprises analyzing at least one word combination used by at least one additional individual.

13. The method of claim 1, wherein said forecasting comprises determining at least one set of words commonly used in a particular context.

14. The method of claim 1, wherein said determining comprises incorporating input from at least one Internet source.

15. The method of claim 1, wherein the confidence value can be indicated via a visual indicator, an audio indicator, a textual change, or a speech change.

16. The method of claim 1, further comprising:
implementing machine-learning capability to learn from at least one previously observed situation and the user's past behavior to adapt the determining step to a user's cognitive tasks and environment.

17. The method of claim 1, wherein the prompt is a speech output or a visual output.

18. The method of claim 1, further comprising:
generating a summary of the user situation and the context information; and
distributing the summary to a pre-configured set of individuals for feedback.

19. The method of claim 1, further comprising:
storing the prompt in a database.

\* \* \* \* \*